United States Patent
Bates et al.

(10) Patent No.: US 9,250,254 B2
(45) Date of Patent: Feb. 2, 2016

(54) BIOSAMPLE CARTRIDGE WITH RADIAL SLOTS FOR STORING BIOSAMPLE CARRIERS AND USING IN AUTOMATED DATA STORAGE SYSTEMS

(71) Applicant: International Business Machines Corporation, Armonk, NY (US)

(72) Inventors: Allen K. Bates, Tucson, AZ (US); Nils Haustein, Mainz (DE); Stephen L. Schwartz, Tucson, AZ (US); Anna W. Topol, Jefferson Valley, NY (US); Daniel J. Winarski, Tucson, AZ (US)

(73) Assignee: International Business Machines Corporation, Armonk, NY (US)

(*) Notice: Subject to any disclaimer, the term of this patent is extended or adjusted under 35 U.S.C. 154(b) by 542 days.

(21) Appl. No.: 13/632,021

(22) Filed: Sep. 30, 2012

(65) Prior Publication Data
US 2014/0094114 A1    Apr. 3, 2014

(51) Int. Cl.
  *H04B 7/24*    (2006.01)
  *G01N 35/00*   (2006.01)
(52) U.S. Cl.
  CPC ........... *G01N 35/00029* (2013.01); *G01N 2035/00089* (2013.01); *G01N 2035/00138* (2013.01)
(58) Field of Classification Search
  USPC .......... 455/39, 41.1, 41.2, 66.1, 67.11, 67.14; 340/572.1, 572.8, 573.1; 360/55
  See application file for complete search history.

(56) References Cited

U.S. PATENT DOCUMENTS

| | | | |
|---|---|---|---|
| 3,859,624 A | 1/1975 | Kriofsky et al. | |
| 4,650,981 A | 3/1987 | Foletta | |
| 4,758,836 A | 7/1988 | Scuilli | |
| 4,941,201 A | 7/1990 | Davis | |
| 5,320,808 A | 6/1994 | Holen et al. | |
| 6,201,474 B1 | 3/2001 | Brady et al. | |
| 6,429,016 B1 | 8/2002 | McNeil | |
| 6,637,473 B2 | 10/2003 | Ganz et al. | |
| 6,699,437 B1 | 3/2004 | Astle | |
| 6,875,405 B1 | 4/2005 | Mathus et al. | |
| 7,118,708 B2 | 10/2006 | Mordekhay | |
| 7,142,987 B2 | 11/2006 | Eggers | |
| 7,382,258 B2 | 6/2008 | Oldham et al. | |
| 7,596,251 B2 | 9/2009 | Affleck et al. | |
| 7,635,246 B2 | 12/2009 | Neeper et al. | |
| 7,660,063 B2* | 2/2010 | Bates et al. | 360/55 |
| 7,663,487 B2* | 2/2010 | Morris et al. | 340/572.1 |
| 7,670,553 B2 | 3/2010 | Babson | |
| 7,922,986 B2 | 4/2011 | Byrnard et al. | |

(Continued)

OTHER PUBLICATIONS

ECMA, "Standardizing Information and Communication Systems," Jun. 2010.

(Continued)

*Primary Examiner* — Thanh Le
(74) *Attorney, Agent, or Firm* — Zilka-Kotab, PC (57) ABSTRACT

Embodiments of the disclosure relate to a biosample cartridge that includes radial slots for storing biosample carriers. The biosample cartridge has the same form factor as data tape cartridges used in automated tape libraries to allow the biosample cartridge to be handled by the same robotic mechanisms that handle the data tape cartridges. One aspect of the disclosure concerns a biosample cartridge that includes a rotatable biosample carrier holder. The biosample carrier holder includes radial slots for receiving biosample carriers which contain biosamples scanned and analyzed by automated tape libraries.

20 Claims, 9 Drawing Sheets

(56) References Cited

U.S. PATENT DOCUMENTS

| | | |
|---|---|---|
| 7,988,644 B2 | 8/2011 | Freeman et al. |
| 7,997,682 B2 | 8/2011 | Silverbrook |
| 8,012,745 B2 | 9/2011 | Glezer et al. |
| 8,337,785 B2 | 12/2012 | Davies et al. |
| 8,640,964 B2 | 2/2014 | Bates et al. |
| 9,207,229 B2 | 12/2015 | Bates et al. |
| 2003/0039591 A1 | 2/2003 | Pham et al. |
| 2003/0087454 A1 | 5/2003 | Schultz et al. |
| 2005/0180894 A1 | 8/2005 | Petroff et al. |
| 2006/0161935 A1 | 7/2006 | Johnson et al. |
| 2009/0117011 A1 | 5/2009 | Morrison |
| 2010/0105074 A1 | 4/2010 | Covey et al. |
| 2011/0076670 A1 | 3/2011 | Boday et al. |
| 2012/0309297 A1 | 12/2012 | Bates et al. |
| 2012/0309298 A1 | 12/2012 | Bates et al. |
| 2014/0018265 A1 | 1/2014 | Bates et al. |

OTHER PUBLICATIONS

Non-Final Office Action from U.S. Appl. No. 13/151,249, dated Feb. 4, 2013.
Final Office Action from U.S. Appl. No. 13/151,249, dated Jul. 17, 2013.
Notice of Allowance from U.S. Appl. No. 13/151,249, dated Sep. 20, 2013.
Non-Final Office Action from U.S. Appl. No. 14/029,667, dated Nov. 15, 2013.
Letter Restarting Period for Response from U.S. Appl. No. 14/029,667, dated Dec. 19, 2013.
Non-Final Office Action from U.S. Appl. No. 14/029,667, dated Jun. 4, 2014.
Final Office Action from U.S. Appl. No. 14/029,667, dated Nov. 19, 2014.
Advisory Action from U.S. Appl. No. 14/029,667, dated Feb. 12, 2015.
Notice of Allowance from U.S. Appl. No. 14/029,667, dated Mar. 30, 2015.
Non-Final Office Action from U.S. Appl. No. 13/151,247, dated Jun. 18, 2014.
Notice of Allowance from U.S. Appl. No. 13/151,247, dated Jan. 20, 2015.
Davies et al., "Engineered Particles Surfaces," Advanced Materials, Wiley-VCH, vol. 10, No. 15, 1998, pp. 1264-1270.
Bates et al., U.S. Appl. No. 13/151,249, filed Jun. 1, 2011.
Bates et al., U.S. Appl. No. 14/029,667, filed Sep. 17, 2013.
Bates et al., U.S. Appl. No. 13/151,247, filed Jun. 1, 2011.
Non-Final Office Action from U.S. Appl. No. 13/151,247, dated May 27, 2015.
Notice of Allowance from U.S. Appl. No. 14/029,667, dated Jul. 29, 2015.
Notice of Allowance from U.S. Appl. No. 13/151,247, dated Nov. 18, 2015.
Bates et al., U.S. Appl. No. 14/929,082, filed Oct. 30, 2015.
Non-Final Office Action from U.S. Appl. No. 14/929,082, dated Dec. 2, 2015.

* cited by examiner

BIOSAMPLE CARTRIDGE WITH RADIAL SLOTS FOR STORING BIOSAMPLE CARRIERS AND USING IN AUTOMATED DATA STORAGE SYSTEMS

CROSS-REFERENCE TO RELATED APPLICATIONS

This application is related to pending and commonly-assigned U.S. patent application Ser. No. 13/151,249, entitled "A Cartridge For Storing Biosample Plates and Use In Automated Data Storage Systems", and application Ser. No. 13/151,247, entitled "A Cartridge For Storing Biosample Capillary Tubes and Use In Automated Data Storage Systems," all of which are hereby incorporated by reference.

FIELD OF THE INVENTION

Embodiments of the invention relate to analytical devices and systems, and more particularly, to a cartridge with radial slots for storing biosample carriers. The cartridge may be stored in the cartridge storage slots of a tape library system and handled by the robotic mechanism of the tape library system.

BACKGROUND

Samples of biological matters are analyzed in bio-assay processes to detect the presence of bacteria, viruses, cancer cells, and other substances of interest. The biological samples may be stored in sample carriers, such as microscope slides and capillary tubes, and analyzed by a biological detection instrument. The detection instrument may record the analysis results of a biosample on a data storage medium such as a computer memory, disk drive, magnetic tape, or compact disk, which may include an identification tag to correlate the biosample with the analysis results.

High-performance computer data storage systems such as optical disc and magnetic tape libraries possess the necessary automation to scan and analyze the biosamples at a very high speed, and tabulate the resulting analysis data. For example, these systems may analyze the biosamples using magnetic tape read-sensors to detect magnetized nanoparticles attached to the biosamples. The biosamples and analysis data may be stored in different locations following the analysis, which make it difficult to correlate the biosamples with the corresponding data when needed. For a large number of biosamples and carriers (e.g., microscope slides and capillary tubes) used to store the biosamples, the task of correlating the biosamples to their data becomes even more complex. It is desirable to exploit the use of automation functions available in data storage library systems to facilitate the correlation and management of biosample carriers and biosample analysis data.

BRIEF SUMMARY OF THE DISCLOSURE

The disclosure relates to storage cartridges that include internal radial slots for holding biosample carriers and have the same form factor as data storage cartridges. The biosample storage cartridges may be handled by the same robotic mechanisms that handle data cartridges in automated data storage library systems. One aspect of the disclosure concerns a biosample cartridge that has an enclosure with a movable door to provide access to a rotatable biosample carrier holder in the enclosure, wherein the biosample cartridge has the same form factor as data tape cartridges used in automated tape libraries. The biosample carrier holder includes radial slots for holding biosample carriers which can be accessed through the movable door of the enclosure. The biosample carriers contain biosamples that may be scanned and analyzed within an automated tape library.

Another aspect of the invention concerns an analytical system that comprises an automated tape library for use with a biosample storage cartridge. The biosample storage cartridge has an enclosure with a movable door to provide access to a rotatable biosample carrier holder in the enclosure. The biosample carrier holder includes radial slots for holding biosample carriers. The biosample carriers contain biosamples that are scanned and analyzed within the automated tape library. The cartridge enclosure has the same form factor as a data tape cartridge used in the automated tape library and can be handled by robotic cartridge-handling mechanism in the automated tape library.

Still another aspect of the disclosure concerns an analytical system that comprises a tape drive and a biosample storage cartridge. The biosample storage cartridge has an enclosure with a movable door to provide access to a rotatable biosample carrier holder in the enclosure. The biosample carrier holder includes radial slots for holding biosample carriers such as microscope slides and capillary tubes. The biosample carriers contain biosamples that may be scanned and analyzed by an analyzer having the same cartridge loader, drive motor, and drive electronics as a tape drive, and this analyzer resides in the automated storage library. The cartridge enclosure has the same form factor as a data tape cartridge used in the tape drive, thus allowing the common use of key tape drive and tape library components in the analyzer.

The details of the exemplary embodiments of the disclosure, both as to its structure and operation, are described below in the Detailed Description section in reference to the accompanying drawings. The Brief Summary is intended to identify key features of the claimed subject matter, but it is not intended to be used to limit the scope of the claimed subject matter.

DETAILED DESCRIPTION OF THE DISCLOSURE

Embodiments of the disclosure relate to a biosample storage cartridge that includes a rotatable holder having radial slots for holding biosample carriers such as microscope glass slides and capillary tubes. The biosamples of the cartridge may be scanned and analyzed by a tape drive in an automated tape library. Such as a tape drive may be modified from a typical tape drive for the purposes of biosample analysis. The cartridge may be handled by the robotic mechanisms of the library and stored in the cartridge storage slots of the automated tape library. The biosample carriers contain biological samples that may be processed and magnetically labeled by electromagnetic tape heads in a write operation. The magnetically labeled biological samples may then be scanned and read by anisotropic magneto-resistive (AMR), giant magnetoresistive (GMR) or tunnel magnetoresistive (TMR) read sensors to detect the presence of target substances or microorganisms in the biological samples.

The biosample storage cartridge has the same form factor as a magnetic tape cartridge used to store data and thus may be conveniently accessed, manipulated, and processed by robotic mechanisms in tape drives and tape libraries. The biosample storage cartridge may be handled through the same library internal-external mail slot as a tape cartridge. The same tape automation mechanisms and processes used in modern tape libraries may be employed for long-term biological-archival storage of the biosamples contained in the biosample storage cartridge.

The radial slots in the biosample storage cartridge may include one or more leaf springs to retain the biosample carriers in place when the cartridge is moved, for example, by a robotic picker in an automated tape library or when the storage cartridge is in shipment. In one embodiment, the rotatable carrier holder includes radial and rectangular slots for receiving biosample carriers in the form of microscope slides. In another embodiment, the rotatable carrier holder includes radial and cylindrical slots for receiving capillary tubes. Exemplary embodiments of the biosample storage cartridge with radial slots are described in detail below with reference to FIGS. 1-5.

Figure 1:
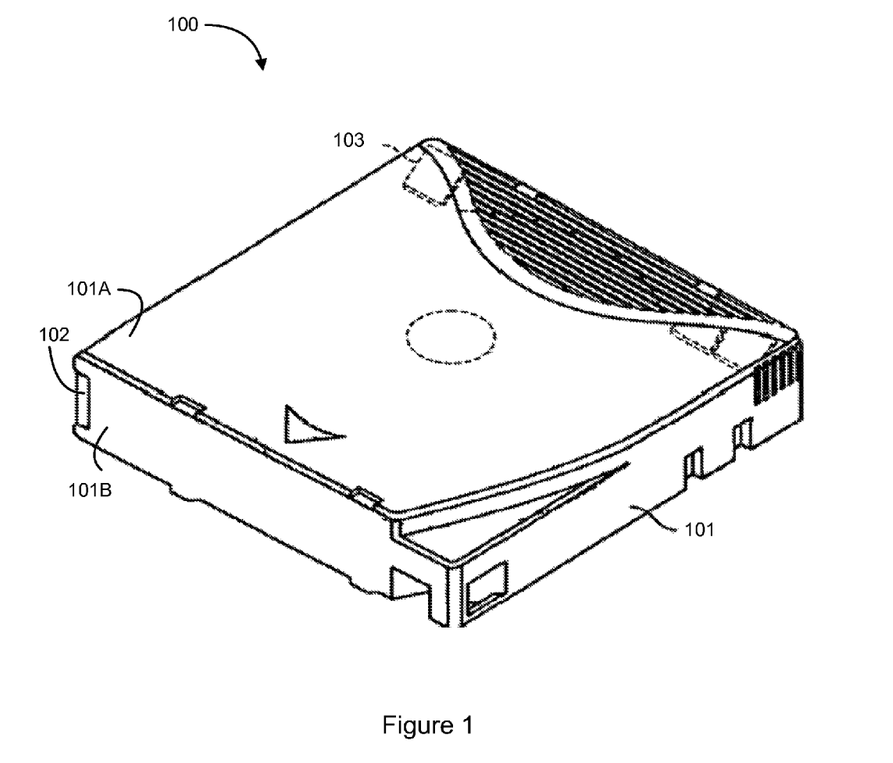
FIG. 1 illustrates an exemplary biosample cartridge for storing biosample carriers, in accordance with an embodiment of the invention.

Referring to the drawings and in particular to FIG. 1, there is illustrated an exemplary biosample storage cartridge 100 which includes internal radial slots for holding biosample carriers. The biosample storage cartridge 100 comprises an enclosure 101 which may include one or more parts assembled together such as top and bottom covers. The cartridge enclosure 101 may have a movable side door 102 that can be slid open, for example by a cartridge access mechanism in a tape drive, to gain access to the interior space of the cartridge 100. Such a tape drive may be adapted to perform an analysis of a biosample stored in a biosample carrier. In one embodiment, the biosample storage cartridge 100 may comprise a top shell 101A and a bottom shell 101B, wherein the top shell 101A is removably affixed to the bottom shell 101B by screws or other fasteners. Alternatively, the biosample storage cartridge 100 may have a front, top, or rear door that is movable to provide access to the biosample carriers in the cartridge.

The biosample storage cartridge 100 may have the same dimensions and exterior form factor as a magnetic tape storage cartridge based on LTO (Linear Tape Open) technology, the IBM TS1140 magnetic tape data storage cartridge, or the Oracle T10000 tape cartridge. In an alternate embodiment, earlier models of IBM single-reel tape cartridges could be used, such as the 3480, 3490, and 3590 tape cartridges. In a data storage cartridge, a data storage media such as a magnetic tape, may be mounted on a tape reel and occupy the space inside the biosample storage cartridge 100 rather than the biosample carriers. Such a tape data storage cartridge may comprise a cartridge brake release button to allow the tape reel to freely rotate once the cartridge is loaded into a data storage drive.

The biosample storage cartridge 100 may further include one or more cartridge memories 103 for storing identification information about the storage cartridge 100, data related to the biosample carriers, and analysis data of the biosamples on the biosample carriers in the cartridge 100. Each cartridge memory 103 may comprise a transponder having a wireless interface, which is retained in the cartridge 100, for example, by being encapsulated by the cartridge when it is assembled in manufacturing. The encapsulation process is understood by those of skill in the art as applied to a single cartridge memory.

Figure 2A:
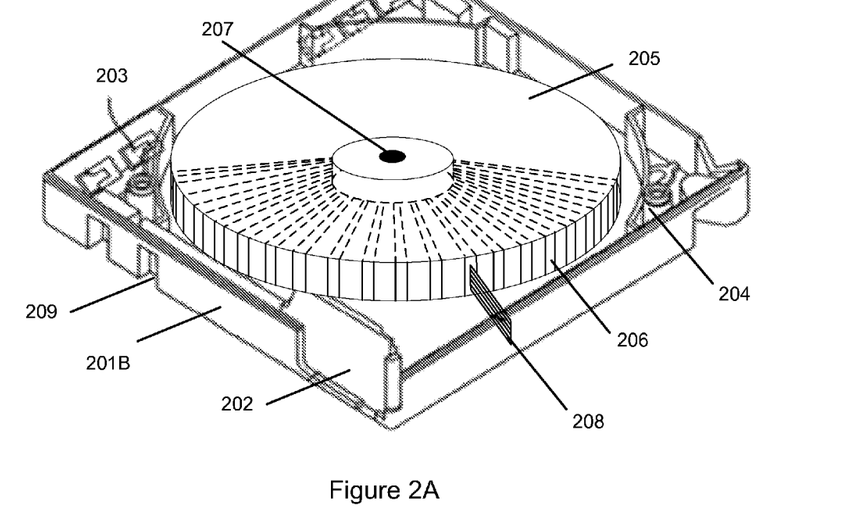
FIG. 2A illustrates a biosample storage cartridge with its cover opened to show a biosample carrier holder that includes radial slots for receiving biosample carriers, in accordance with an embodiment of the invention.

FIG. 2A illustrates a biosample storage cartridge 200 with its top cover removed to show a biosample carrier holder for holding biosample carriers, in accordance with an embodiment of the invention. Bottom cover 201B may be held to a top cover (not shown) by mating pins 204 and screws. The storage cartridge 200 comprises a rotatable carrier holder 205 for holding biosample carriers 208. The rotatable biosample carrier holder 205 may be attached to the bottom cover 201B by a center pin 207 which allows the biosample carrier holder 205 to freely rotate around the center pin 207. In one embodiment, the biosample carrier holder 205 has the form factor of a data tape reel in a data storage tape cartridge.

Figure 2B:
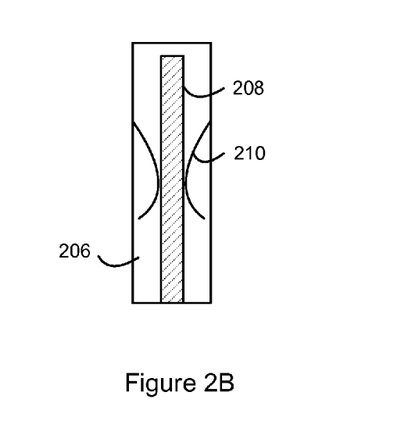
FIG. 2B illustrates a biosample storage slot with leaf springs attached to the its interior walls for retaining a biosample carrier in the slot when the biosample storage cartridge is in motion, in accordance with an embodiment of the invention.

The biosample carrier holder 205 includes radial slots 206 for holding biosample carriers 208. The biosample carriers 208 may be rectangular microscope slides of glass that are commonly used for biological and chemical analysis. Each of the radial slots 206 may have one or more leaf springs 210 attached to the inside walls of the radial slots 206 to retain the biosample carriers 208 in the radial slots 206, as illustrated in FIG. 2B. The leaf springs 210 prevent the biosample carriers 208 from falling out of the radial slots 206 when the biosample storage cartridge 200 is being moved, for example, by the robotic arm of an automated tape library system. The robotic arm may grasp the cartridge 200 at notches 209 in the cartridge cover 201B. An opening in bottom cover 201B, which is normally covered by movable door 202 when the biosample cartridge 200 is not in use, provides access to the biosample carriers 208 in the cartridge 200. Each radial slot 206 and biosample carrier 208 may include a barcode or QR (Quick Response) code for identification, which may be read by a barcode reader or QR reader in an automated tape library as described with reference to FIG. 7.

FIG. 2A further illustrates one or more memory components 203 in the biosample storage cartridge 200 for storing data related to the cartridge 200 and its contents. This data may include, for example, identification information on the cartridge 200, the biosample carriers 208, and the biological samples in the carriers 208. The cartridge memory 203 may further include analysis data on the biological samples in the biosample storage cartridge 200 and relevant dates such as when the biosamples were created and analyzed. The cartridge memory 203 may be in communication with a wireless communication interface to send information to and receive information from a remote transceiver, for example, in a tape library system that handles the biosample storage cartridge 200.

Figure 3:
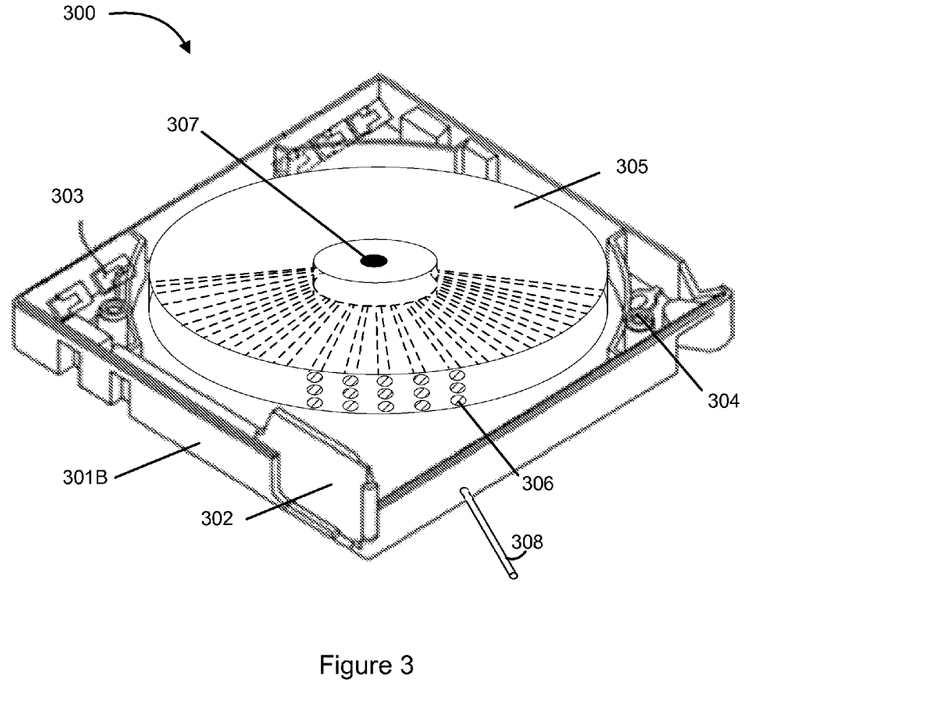
FIG. 3 illustrates a biosample storage cartridge with its cover opened to show a biosample carrier holder that includes radial cylindrical slots for receiving biosample capillary tubes, in accordance with an embodiment of the invention.

FIG. 3 illustrates another embodiment of a biosample storage cartridge 300 in which biosample carrier holder 305 includes radial cylindrical slots 306 for holding biosample carriers in the form of capillary tubes 308. In one embodiment, the diameter of the cylindrical slots 306 may be slightly larger than the diameter of the capillary tubes 308 to snugly accommodate the capillary tubes 308 and firmly retain the capillary tubes 308 in the cylindrical slots 306 by friction. For example, the capillary tubes 308 may have a diameter of 1.0 mm and the diameter of the cylindrical slots 306 is slightly larger than 1.0 mm, e.g., 1.1 mm. In an alternate embodiment, the material containing the radial cylindrical slots 306 is elastic, such as a polymer or elastomer, and the diameter of the radial cylindrical slots 306 is slightly smaller than the diameter of the capillary tubes 308, ranging from 0.90 mm to 1.0 mm. The biosample carrier holder 305 of the cartridge 300 may be rotatably attached to an enclosure bottom cover 301B at center pin 307. The bottom cover 301B may be coupled to a top cover (not shown) by alignment pins 304. The bottom cover 301B further includes a sliding door 302 to provide access to the biosample carriers 308 and one or more memories 303 to store biosample data.

The inside and outside of a biosample storage cartridges 200 and 300 may have a coating of a thin nanocomposite film that comprises titanium dioxide and nitrogen to eradicate bacteria which might try to escape the cartridges. Titanium dioxide based coatings can eradicate bacteria after activation with UV light. The addition of nitrogen to these coatings enables photons available in visible light to be utilized to activate the surface and eradicate bacteria. Alternately, this coating may comprise nickel-alloy, copper-alloy, zinc oxide, or a film comprising silver particles in a fluoropolymer matrix enhanced by depositing an additional very thin layer of gold or brass clusters.

In another embodiment, the biosample storage cartridges 200 and 300 may have the same form factor as a dual reel cartridge, such as the IBM 3570 cartridge. A dual reel cartridge includes a supply reel and a take-off reel and the tape is fed between the two reels. Such a biosample storage cartridge comprises a rotary biosample carrier holder 205 or 305 in the space occupied by the two tape reels instead of the space occupied by a single tape reel, as described with reference to FIGS. 1-2.

Figure 4:
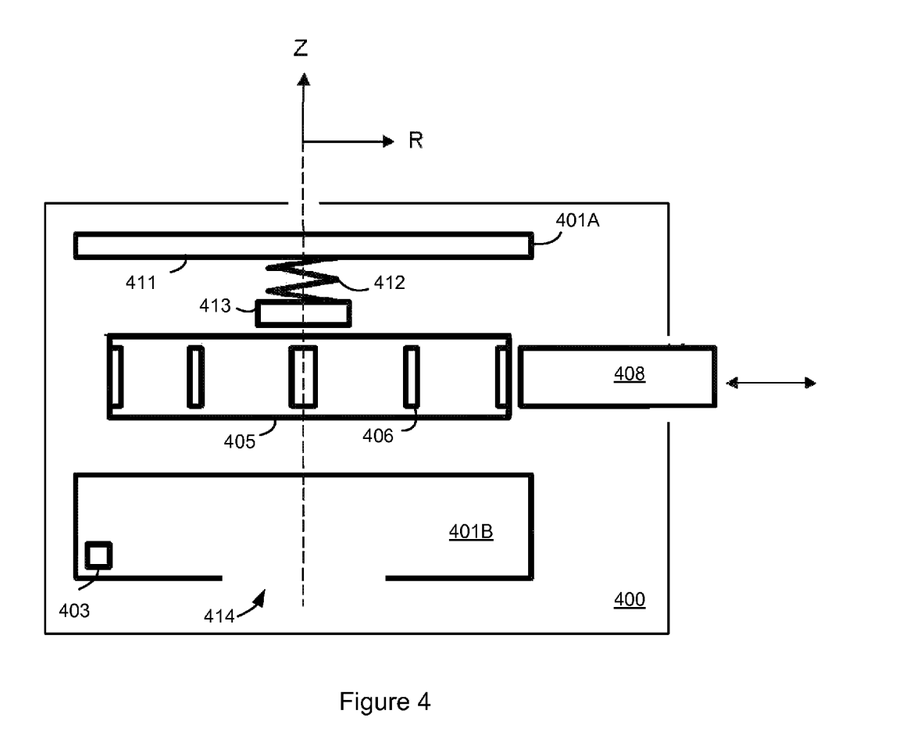
FIG. 4 illustrates an example biosample storage cartridge which includes a spring and brake mechanism for controlling the movement of the biosample carrier holder to access selected radial slots in the holder, in accordance with an embodiment of the invention.

FIG. 4 illustrates an example biosample storage cartridge 400 which includes a spring and brake mechanism for controlling the movement of the biosample carrier holder to access selected radial slots in the holder, in accordance with an embodiment of the invention. The biosample storage cartridge 400 includes a top cover 401A and bottom cover 401B which together form the cartridge enclosure. Bottom cover 401B may include one or more cartridge memory 403 for storing biosample, cartridge, and carrier data and wirelessly communicating with an external device. Rotatable biosample carrier holder 405 includes multiple radial slots 406 for holding biosample carriers 408, for example, in the form of microscope slides. The biosample carrier holder 405 may be controllably rotated around axis Z by a biosample access drive that reaches the biosample carrier holder 405 through an opening 414 in the bottom cover 401B. Such a biosample access drive is described below with reference to FIG. 5.

In one embodiment, the movement of the biosample carrier holder 405 may be controlled by spring 412 and brake 413. One end of the spring 412 is attached to the interior surface 411 of the top cover 401A. The other end of the spring 412 is attached to the brake 413. The brake 413 is disengaged from the rotatable biosample carrier holder 405 when a biosample access drive, such as drive 520 illustrated in FIG. 5, activates and rotates the biosample carrier holder 405 to access a target biosample carrier 408 in the biosample cartridge 400. When the biosample access drive 520 no longer rotates the biosample storage holder 405, the brake 413 and spring 412 mechanism applies pressure on the biosample carrier holder 405 to prevent unwanted movement of the biosample carrier holder 405.

Figure 5:
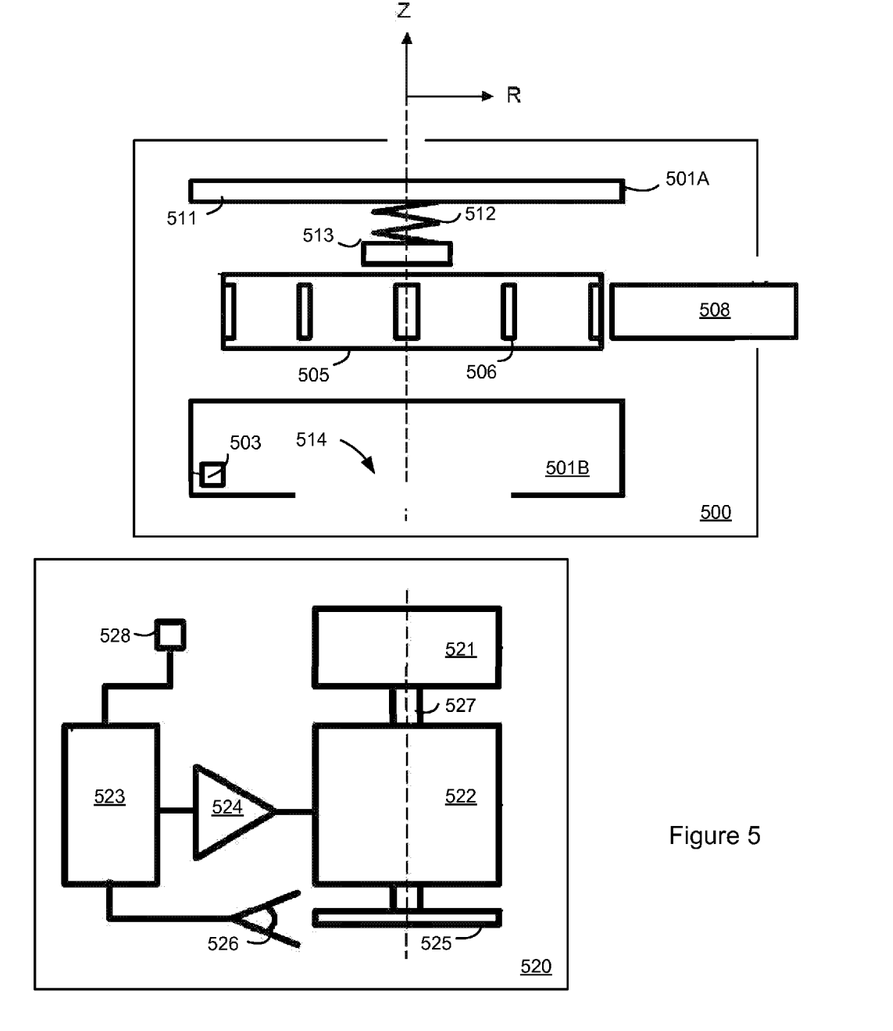
FIG. 5 illustrates a biosample access drive for controllably rotating a biosample storage cartridge with radial slots, in accordance with an embodiment of the invention.

FIG. 5 illustrates an example biosample access drive 520 for controllably rotating a biosample storage cartridge 500, in accordance with an embodiment of the invention. The biosample access drive 520 may be the same drive that accesses a data storage tape cartridge in a tape drive or another drive designed for accessing the biosample storage cartridge 500. The biosample access drive 520 includes a motor 522 and a clutch 521 that is attached to the motor 522 by motor shaft 527. A control microprocessor 523 may send appropriate signals to the motor 522, via amplifier 524, to start, stop, and reverse the rotation of the clutch 521. The clutch 521 is in contact with the biosample carrier holder 505 through opening 514 in the bottom cover 501B, and thus rotates the biosample carrier holder 505 under the control of microprocessor 523 to access a selected biosample carrier 508 from its radial storage slot 506.

The biosample access drive 520 may include a rotary encoder 525 attached to motor 522 to assist with information on the current position of the biosample carrier holder 505. This positional information may be sensed by a sensor 526, e.g., an optical sensor, and sent to the microprocessor 523 of the biosample access drive 520. The microprocessor 523 is further in communication with the cartridge memory 503 in the biosample storage cartridge 500, via wireless transponder 528 coupled to the microprocessor 523. Thus, the microprocessor 523 has access to the latest information related to the biosample storage cartridge 500, the biosample carriers 508, and data on the biosamples that are currently in the biosample carriers 508.

Figure 6:
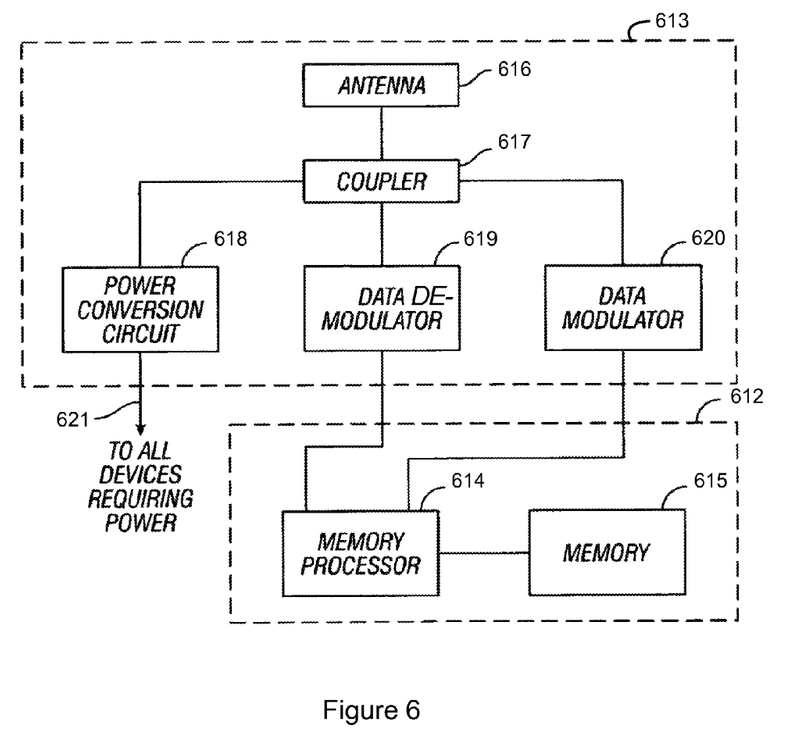
FIG. 6 illustrates a block diagram of a memory component and a wireless communication interface, which may be part of a biosample storage cartridge, for storing and transferring information related to the cartridge and its contents, in accordance with an embodiment of the invention.

FIG. 6 illustrates a block diagram of the functional components of a cartridge memory 612 and wireless communication interface 613, which may be part of a biosample storage cartridge memory, e.g., the cartridge memory 503 in the biosample storage cartridge 500. The memory component 612 may include information about the biosample storage cartridge 500, biosample carriers 507 stored in the biosample storage cartridge 500, and biosamples on the biosample carriers 508. In one embodiment, the memory component 612 may comprise a nonvolatile memory 615, such as an electrically erasable programmable read-only memory (EEPROM), a phase-change memory, flash memory, NOR memory, or a NAND memory arranged to operate in a low power environment.

Memory component 612 may comprise a memory processor 614, such as logic or a microprocessor chip, for example, an Intel Pentium™ chip arranged to operate in a low power environment, such as a portable computer. The memory processor 614 may have computer readable program code embodied therein, including suitable security and encryption/decryption algorithms, and the logic for accessing and operating the memory component 612. The nonvolatile storage 615 may comprise a separate chip attached to the logic or memory processor 614, or may comprise a portion of the same chip. The computer readable program code may be stored in a nonvolatile internal memory of the processor 614 or in the nonvolatile memory 615, and loaded into the processor 614. Alternatively, the memory component 612 may be operated by a control system or processor of an analytical system that uses the biosample storage cartridge 500.

In the illustrated embodiment, the wireless communication interface 613 may be a radio frequency (RF) wireless interface. An example of an RF wireless interface is described in U.S. Pat. No. 4,941,201. A high frequency inductive wireless interface may also be employed, which is of sufficiently high frequency so that it does not adversely affect magnetic storage media that may be present in a tape library system that handles the biosample storage cartridge 500. Examples of high frequency inductive wireless interfaces are described in U.S. Pat. No. 4,650,981, U.S. Pat. No. 4,758,836, and U.S. Pat. No. 3,859,624.

The wireless communication interface 613 includes an antenna 616 for receiving an RF signal from an RF interface of either a tape drive modified to perform bio-analysis or a robotic picker that moves a biosample storage cartridge, e.g., cartridge 500, in a tape library system. The antenna 616 may be positioned at an angle in the range of 30-60 degrees for optimal reception of the RF signal, e.g., at 45 degrees as shown for the cartridge memory 503 of FIG. 5, by either the tape library 700 in FIG. 7 or a modified tape drive 800 in FIG. 8. The antenna 616 may be a quarter wave antenna, a fractal antenna, or the inductor of an inductor-capacitor oscillator.

A coupler 617 supplies the received signal to a power conversion circuit 618 and to a data demodulator 619. The power conversion circuit 618 converts the received signal to a power current, supplying the current on line 621 to all devices on the biosample storage cartridge 500, including the memory component 612, the data demodulator 619, and a data modulator 620. The received signal from antenna 616 may be encoded.

The data demodulator 619 receives the incoming coded signal from coupler 617 and demodulates the signal to provide data signals to the memory component 612 and for writing to memory 615. Data signals being read from memory 615 and memory component 612 are provided to the data modulator 620 which encodes the signals for transmission by coupler 617 and antenna 616 to an RF interface, which may be in either the robotic picker of the tape library system that handles the biosample storage cartridge 500 or in the tape drive modified to perform bio-analysis.

Figure 7:
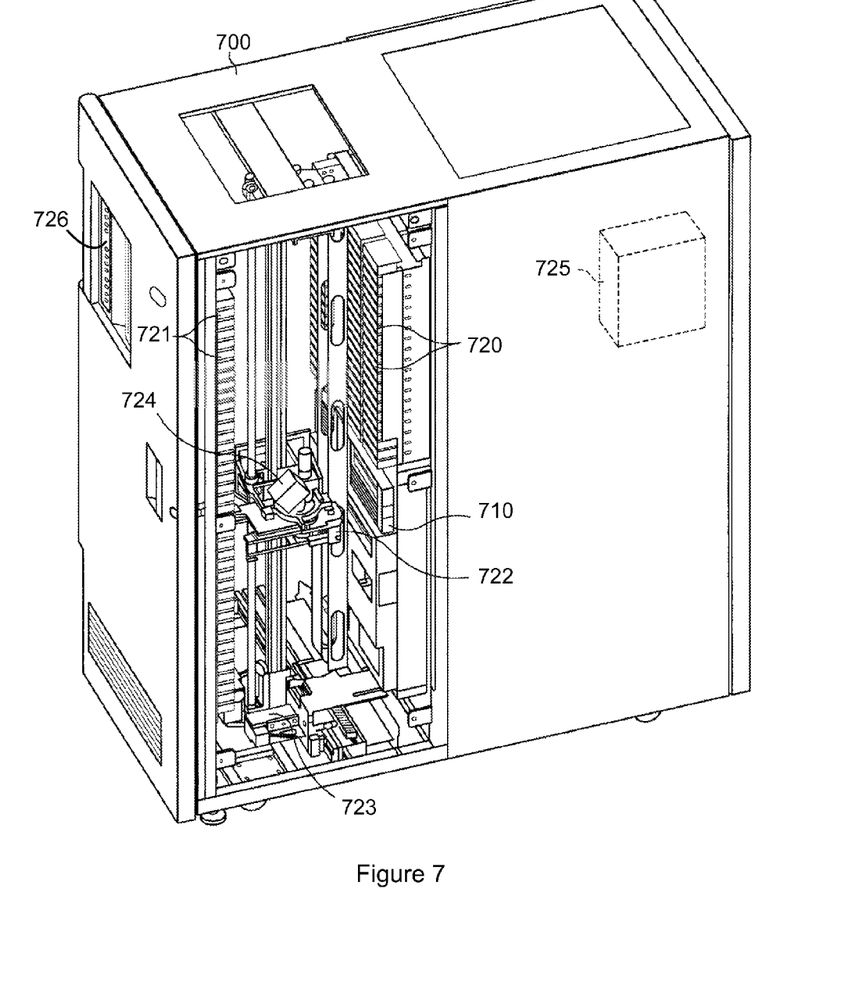
FIG. 7 illustrates an automated data storage tape library that may be used with the biosample storage cartridge having radial slots, in accordance with an embodiment of the invention.

FIG. 7 illustrates an automated data storage tape library 700 that may be used with the biosample storage cartridge shown in FIGS. 1-6, in accordance with an embodiment of the invention. The data storage tape library 700 is an automated tape library that may include a number of tape drives 710 for reading and writing data on magnetic tape media, such as single-reel or two-reel magnetic tape cartridges. Examples of the library 700 include IBM TS3400™ and TS3500™ Tape Libraries, IBM TotalStorage™ 3494 Tape Libraries, and IBM 3952™ Tape Frames Model C20, which store magnetic tape cartridges and use IBM TS1140™ tape drives. Other examples of the library 700 include IBM TS3310™ and TS3100/3200™ tape libraries which store magnetic tape cartridges and use IBM LTO (Linear Tape Open) tape drives.

Tape drives modified to perform bio-analysis accept cartridges 100, 200, 300, 400 and 500 from the robotic picker, withdraw a biosample carrier 208 through a cartridge door, e.g., door 102 of cartridge 100, and perform the bio-analysis.

A plurality of cartridges 720 are stored in banks or groups of cartridge storage slots 721. Cartridges 720 may comprise tape media for data storage, tape substrate for biosamples, or biosample carriers 208, 308, 408 and 508 for bio-analysis. Tape media may encompass a variety of media, such as that contained in magnetic tape cartridges, magnetic tape cassettes, and optical tape cartridges, in various formats. For universal reference to any of these types of media, the terms "tape media" or "media" are used herein, and any of these types of containers are referred to as "tape cartridges" or "cartridges" herein. An access robot 723, including a cartridge picker 722 and a barcode or QR-code reader 724 mounted on the cartridge picker 722, transports a selected cartridge 720 between a cartridge storage slot 721 and a drive 710. Barcode or QR-code reader 724 is mounted directly on picker 722 so that the library 700 can check the barcode or QR-code on cartridge 720 before picking the cartridge and transporting it to a drive 710, storage slot 721, or import/export mail slot 726.

The automated tape library 700 further has a library controller 725 which includes at least one microprocessor. The library controller 725 may serve to provide an inventory of the cartridges 720 and to control the library 700. Typically, the library controller 725 has suitable memory and data storage capability to control the operation of the library 700. The library controller 725 controls the actions of the access robot 723, cartridge picker 722, and barcode or QR-code reader 724. Barcode or QR-code reader 724 may read a barcode or QR-code from a cartridge such as cartridge 200. Cartridge storage slot 721 may have a barcode and/or QR-code to designate an empty storage slot, for inventory purposes.

The library controller 725 is interconnected through an interface to one or more host processors, which provides commands requesting access to a particular biosample carrier or a biosample cartridge in a particular cartridge storage slot. A host, either directly or through the library controller, controls the actions of the drives 710 which either perform data IO with tape media or, if suitably modified, perform bio-analysis on biosamples extracted from the biosample carriers. Commands for accessing data or locations on the tape media and biosample carriers, and information to be recorded on or to be read from selected tape media and biosample carriers, are transmitted between the drives 710 and the host. The library controller 725 is typically provided with a database for locating the cartridges 720 in the appropriate storage slots 721 and for maintaining the cartridge inventory.

Library 700 also includes an import/export mail slot 726, which is a portal allowing cartridges 720 to be entered into or removed from library 700. Since cartridges 720 have a generally identical exterior dimensions regardless of whether they hold data tape or biosample tubes, cartridges 720 may enter library 700 through import/export mail slot 726, picked up by picker 722 and transported to either cartridge-storage slot 721 or drives 710. Drives 710 would have a common cartridge loader mechanism, whether the drive is a data drive or a bio-analysis drive, because of cartridges 720 having identical exterior dimensions. Similarly, picker 722 may pick a cartridge 720 from a drive 710 or cartridge-storage slot 721 and place it in import/export mail slot 726 for removal from library 700. In an alternate embodiment, biosample cartridges 720 are a different color from cartridges containing digital data, as well as containing information regarding their intended purpose in cartridge memories, e.g., memory 503. In yet another embodiment, data cartridges are labeled with barcodes, and biosample cartridges are labeled with QR-codes.

Figure 8:
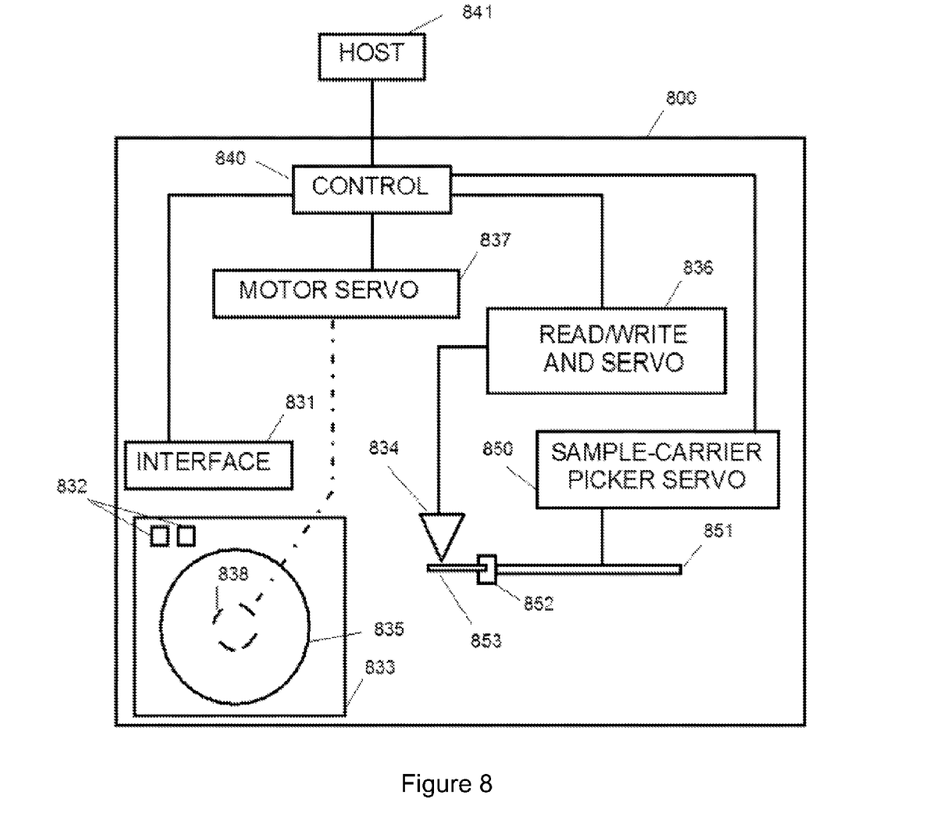
FIG. 8 illustrates a block diagram of the main components of a modified data storage tape drive that may be used for analyzing a biosample and storing biosample identification and analysis data, in accordance with an embodiment of the invention.

FIG. 8 illustrates a block diagram of the functional components in a tape drive that may be used for analyzing a biosample and storing biosample identification and analysis data, in accordance with an embodiment of the invention. The magnetic tape drive 800 comprises a memory interface 831 for reading information from and writing information to one or more of the cartridge memories 832 of the magnetic tape cartridge 833, for example, in a contactless manner.

A read/write servo system is provided for reading and writing information to the data storage media, such as magnetic tape, or nanoparticles attached to the biosamples, and may comprise a read/write head 834 coupled to a servo system for moving the read/write head 834 laterally across biosample plate 853. The servo system may comprise a read/write and servo control 836 and a cartridge motor system 837 which activates motor 838 to move biosample carrier holder 835 of a biosample cartridge 833. A cartridge gripper 852 of sample-carrier picker 851 can grasp a rectangular slide or capillary tube carrier 853 that contains a biosample from cartridge 833 and move the biosample carrier 853 longitudinally across the write elements and read sensors of head 834. It is biosample picker control 850 which controls gripper 852 of biosample-carrier picker 851. The biosample picker servo 850 controls the operation of the sampler-carrier picker 851 to move the sample 853 across the read/write head 834 at a desired velocity. The read/write and servo control 836 may determine the location of the read/write head 834 with respect to biosample carrier 853.

In one example, the read/write head 834 and read/write and servo control 836 employ servo signals from a servo track on biosample carrier 853 to determine the relative location of the read/write head 834 to biosample carrier 853. The read/write head 834 and read/write and servo control 836, motor servo 837, and biosample-carrier picker servo 850 may comprise hardware elements and may comprise any suitable form of logic, including a processor operated by software, or microcode, or firmware, or may comprise hardware logic, or a combination.

A control system 840 communicates with the memory interface 831 to cartridge memories 832, a read/write system, e.g., at read/write and servo control 836, motor servo 837, and biosample-carrier picker servo 850. The control system 840 may comprise any suitable form of logic, including a processor operated by software, or microcode, or firmware, or may comprise hardware logic, or a combination thereof. The control system 840 typically communicates with one or more host systems 841, and operates the data storage drive 800 in accordance with commands originating at a host. Alternatively, the data storage drive 800 may form part of a subsystem, such as a library, and may also receive and respond to commands from the subsystem.

As illustrated, the data storage drive 800 provides information to a cartridge memory 832 of the magnetic tape cartridge 833, and provides data to the cartridge memories 832 of the magnetic tape cartridge 833.

In one embodiment, the data storage tape drive 800 may function as an analytical system for scanning the biosample carrier 853 and analyzing biological samples stored in the biosample carriers 853 to detect the presence of target antigens or substances. The magneto-resistive (MR) heads of the read/write head 834 in data storage drive 800 may act as the scanners for reading data from the biosamples. Write elements of read/write head 834 may magnetize nanoparticles used to tag the biosamples which are subsequently read or detected by the AMR, GMR, or TMR magnetoresitive read sensors. For example, a read/write head 834 may be used to detect micro-organisms and antigens that are attached to magnetized nanoparticles.

Read-write head 834 may scan a large number of biosamples deposited on biosample carrier 853 at high speed. The tape drive 800 electronics may then process the signals from the read-write head 834 to detect the presence of target micro-organisms or antigens in the biosamples. Such as bioassay process is described, for example, in the commonly-assigned U.S. patent application entitled "Detection Of Analytes Via Nanoparticle-Labeled Substances With Electromagnetic Read-Write Heads", Ser. No. 12/888,388, herein incorporated by reference in its entirety.

Figure 9:
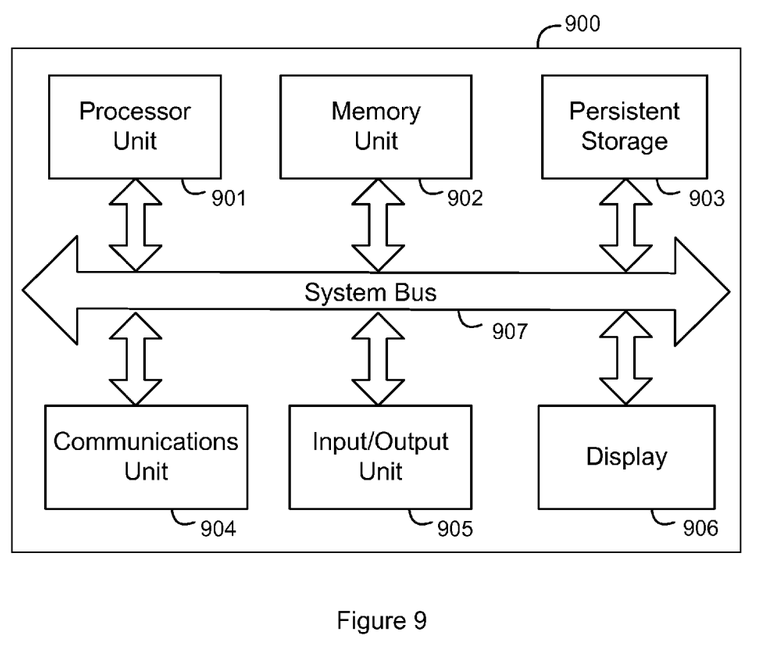
FIG. 9 illustrates a block diagram of the main components in a computer, which may be incorporated into a tape drive, a data storage tape library, and a cartridge memory to provide control and processing functions, in accordance with an embodiment of the invention.

FIG. 9 illustrates a block diagram of a representative computer system, some of which may be incorporated in a data storage tape library and a cartridge memory to provide control and processing function, for providing aspects of the disclosure. Computer system 900 includes a processor 901, a memory 902, a persistent storage 903, a communication interface 904, an input/output unit 905, a display 906 and a system bus 907. Computer programs are typically stored in persistent storage 903 until they are needed for execution by an operating system running in memory 902. Persistent storage 903 may comprise one or more hard disk drives and multiple hard disk drives may be organized into a RAID, CD (Compact Disk) drives, DVD (Digital Versatile Disk) drives, BD (Blu-Ray) drives, SSD (Solid State Drives), and solid state memory. At that time, the programs are brought into the memory 902 so that they can be directly accessed by the processor 901. The processor 901 selects a part of memory 902 to read and/or write by using an address that the processor 901 gives to memory 902 along with a request to read and/or write. Usually, the reading and interpretation of an encoded instruction at an address causes the processor 901 to fetch a subsequent instruction, either at a subsequent address or some other address. The processor 901, memory 902, persistent storage 903, communication interface 904, input/output unit 905, and display 906 interface with each other through the system bus 907.

The subject matter described above is provided by way of illustration only and should not be construed as limiting. Various modifications and substitutions of the described components and operations can be made by those skilled in the art without departing from the spirit and scope of the present disclosure defined in the following claims, the scope of which is to be accorded the broadest interpretation so as to encompass such modifications and equivalent structures.

What is claimed is:

1. A cartridge for storing biosample carriers, comprising:
   an enclosure including a movable door to provide access to inside the enclosure and having the same form factor as a data tape cartridge used in an automated tape library; and
   a rotatable biosample carrier holder disposed in the enclosure and having a plurality of radial slots for receiving the biosample carriers, the biosample carriers including biosamples that are scanned and analyzed by the automated tape library.

2. The cartridge of claim 1, wherein the biosample carrier holder is controllably rotated to allow access to a selected biosample carrier.

3. The cartridge of claim 1, wherein the cartridge has a form factor selected from the group consisting of an LTO type cartridge, a TS1140 tape cartridge, a T10000 tape cartridge, and an optical disk cartridge.

4. The cartridge of claim 1, wherein the biosample carriers are microscope slides.

5. The cartridge of claim 4, wherein each of the microscope slides includes a plurality of trenches on a surface of said each microscope slide for holding a biological sample.

6. The cartridge of claim 1, wherein the biosample carriers are capillary tubes.

7. The cartridge of claim 1, wherein each of the radial slots includes a plurality of leaf springs for retaining a respective biosample carrier in position.

8. The cartridge of claim 1, wherein an interior of the radial slots is coated with diamond-like carbon to mitigate sliding friction.

9. The cartridge of claim 1, wherein the biosample carrier holder and interior of the enclosure are coated with an antibacterial compound to mitigate biosample escaping.

10. The cartridge of claim 1, wherein each of the biosample carriers includes a barcode for identifying said each biosample carrier.

11. The cartridge of claim 1, wherein each of the radial slots includes a barcode for identifying said each radial slot.

12. The cartridge of claim 1, further comprising a spring and brake mechanism for controlling movement of the biosample carrier holder.

13. The cartridge of claim 1, further comprising a memory module for storing biosample data and identification data of the biosample carriers and radial slots.

14. The cartridge of claim 13, further comprising a wireless communication interface coupled to the memory module for sending data to and receiving data from the automated tape library.

15. The cartridge of claim 13, wherein the memory module comprises a nonvolatile memory selected from the group consisting of electrically-erasable programmable read-only memory, phase-change memory, flash memory, NOR memory, and NAND memory.

16. The cartridge of claim 1, wherein a biosample access drive rotates the biosample carrier holder through an opening in the enclosure.

17. The cartridge of claim 16, wherein the biosample access drive includes a rotary encoder to provide information on a position of the biosample carrier holder.

18. The cartridge of claim 16, wherein the biosample access drive includes a first wireless communication interface for communicating with a second wireless communication interface in the cartridge.

19. An analytical system comprising:
   an automated tape library;
   a cartridge comprising an enclosure including a movable door to provide access to inside the enclosure and having the same form factor as a data tape cartridge used in the automated tape library; and
   a rotatable biosample carrier holder disposed in the enclosure and having a plurality of radial slots for receiving the biosample carriers, the biosample carriers including biosamples that are scanned and analyzed by the automated tape library.

20. An analytical system comprising:
   a tape drive; and
   a cartridge comprising an enclosure including a movable door to provide access to inside the enclosure and having the same form factor as a data tape cartridge used in the tape drive; and
   a rotatable biosample carrier holder disposed in the enclosure and having a plurality of radial slots for receiving the biosample carriers, the biosample carriers including biosamples that are scanned and analyzed by the tape drive.

* * * * *